(12) United States Patent
D'Alessandro et al.

(10) Patent No.: US 6,767,324 B2
(45) Date of Patent: Jul. 27, 2004

(54) EPICARDIAL COOLED STABILIZER FOR BEATING HEART SURGERY

(75) Inventors: David A. D'Alessandro, New York, NY (US); Mehmet C. Oz, Cliffside Park, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/966,237

(22) Filed: Sep. 28, 2001

(65) Prior Publication Data

US 2003/0065372 A1 Apr. 3, 2003

(51) Int. Cl.⁷ ............................................. A61B 17/00
(52) U.S. Cl. ..................... 600/205; 600/201; 600/231; 600/235
(58) Field of Search .................. 604/174, 178; 600/205, 204; 607/96, 104, 105; 606/231, 232, 233, 235, 201

(56) References Cited

U.S. PATENT DOCUMENTS

| 6,007,486 A | * | 12/1999 | Hunt et al. ................. 600/205 |
| 6,036,641 A | * | 3/2000 | Taylor et al. ............... 600/231 |
| 6,287,326 B1 | * | 9/2001 | Pecor ......................... 607/105 |
| 6,406,424 B1 | * | 6/2002 | Williamson et al. ........ 600/201 |
| 6,447,443 B1 | * | 9/2002 | Keogh et al. ................ 600/37 |

* cited by examiner

*Primary Examiner*—Cary E. O'Connor
*Assistant Examiner*—Candice C. Melson
(74) *Attorney, Agent, or Firm*—William H. Dippert; Reed Smith LLP

(57) ABSTRACT

An epicardial cooled stabilizer system is useful for surgical or laparoscopic applications, especially beating heart surgery. The system comprises a stabilizer connected to a cooler/pump where coolant flows into tubing at the distal end of the stabilizer. The tubing is positioned at a surgical site to enhance traction and minimize trauma.

35 Claims, 4 Drawing Sheets

EPICARDIAL COOLED STABILIZER FOR BEATING HEART SURGERY

FIELD OF THE INVENTION

This invention relates generally to methods and devices for performing surgical procedures. More particularly, this invention relates to a device useful for coronary revascularization and laparoscopic surgery. The device comprises a system which uses cooled instruments to grasp tissue.

BACKGROUND OF THE INVENTION

In coronary artery disease, the build up of artherosclerotic plaque on the inner walls of the coronary arteries causes a narrowing or a complete closure of these arteries, resulting in insufficient blood flow to the heart. This condition has become one of the most common life threatening medical problems facing older men and women.

A number of approaches have been developed for treating coronary artery diseases. In less severe cases, it is often sufficient to treat the symptoms with pharmaceuticals and life style modification to lessen the underlying causes of the disease. In more severe cases, a coronary artery blockage can often be treated using endovascular techniques, such as balloon angioplasty, atherectomy, laser or hot tip ablation, stents, and the like.

It is known that long-term relief from coronary artery disease and improved longevity may be achieved through complete revascularization of a patient who suffers from coronary artery stenosis or infarction of the myocardium. Revascularization by coronary artery bypass grafting (CABG) has long been the gold standard of total revascularization. In particular, a CABG procedure in which the left internal mammary artery (LIMA) is anastomosed to the left anterior descending artery (LAD) is well accepted as providing a superior survival rate. However, conventional CABG procedures have significant complication risks which limit their ultimate efficacy. Conventional CABG procedures require the patient to be placed on cardiopulmonary bypass (CPB) support, which requires systemic heparinization and cardiopulmonary arrest.

It is well known that use of CPB produces an exaggerated inflammatory response which may contribute to postoperative end-organ dysfunction. Furthermore, use of CPB has been associated with an increased risk of intraoperative stroke and other embolic complications. CPB also requires systemic heparinization (blood thinning) which contributes to excessive intraoperative and postoperative bleeding. In addition, methods which stop the heart for surgical grafting may contribute to decreased postoperative cardiac function and increase the likelihood of cardiac arrhythmias.

For these reasons, less invasive means of revascularizing the heart have been developed and employed. Consequently, advanced catheter-based therapies, and percutaneous transluminal coronary angioplasty (PTCA) in particular, have risen in popularity to provide less invasive means for treating coronary artery stenosis. These methods have the advantage of being less traumatic and require a shorter recovery time. However, they are not without their own limitations. It is known that PTCA carries significantly higher restenosis and reintervention rates than a CABG procedure for the LAD. The LAD provides the majority of blood flow to the left ventricle, which is responsible for cardiac output to the vital organs. About 80–90% of patients suffering from symptomatic artherosclerosis require revascularization of the LAD, but multi-vessel disease is often present. Accordingly, the use of catheter-based therapies alone to provide complete revascularization is limited in many cases.

New techniques have been developed which allow surgical revascularization without the need for cardiac arrest or CPB. Approximately 20% of coronary revascularization surgery is currently performed without the use of extracorporeal circulation. Such surgeries, referred to as "beating heart" or "off pump" operations, also known as "OPCAB", require various means of cardiac stabilization to allow precise vascular anastomoses. Often pharmacological manipulation is combined with external compression stabilizers to further stabilize the operative field. However, this can result in hemodynamic fluctuations which prevent successful completion of these procedures. Furthermore, anastomoses without cardioplegic arrest can lead to regional ischemia as blood flow to functioning myocardium is temporarily occluded.

Topical hypothermia has been employed as an adjunct to ischemic arrest to enhance myocardial protection. However, this has largely been abandoned as extreme hypothermia provides little advantage when used in addition to cardioplegic arrest. In contrast, regional hypothermia may have a significant benefit when applied to non-arrested, functional myocardium.

Certain stabilizers are known to be useful in the OPCAB procedures described above. However, there is a need to have a more effective stabilizer, especially one useful in beating heart surgery.

OBJECTS OF THE INVENTION

It is an object of this invention to provide a device useful for surgical procedures, particularly surgery on a beating heart.

It is also an object of this invention to provide a device that increases the efficacy of cardiac or laparoscopic surgical procedures.

It is a further object of this invention to provide a device that is readily available, efficient, and inexpensive.

It is a yet further aspect of the invention to provide a apparatus for surgical applications comprising a longitudinal member capable of cooling tissue.

These and other objects of the invention will become more apparent from the discussion below.

SUMMARY OF THE INVENTION

This invention relates to a stabilizer device especially useful in surgical procedures, especially the revascularization of coronary arteries. The stabilizer device comprises a longitudinal member having a cooling member at its distal end, which cooling member is intended to be placed in a position to surround a surgical site. The cooling member and optionally the longitudinal member comprise tubing or one or more lumens through which coolant flows. The temperature of the coolant is sufficiently low that the outer surface of the cooling member and the area adjacent to and within the surgical site is effectively cooled, preferably to a temperature approaching 0° C., for example, to a temperature where the cooling member outer surface will grasp tissue due to contact between the outer surface and the tissue. The cooling temperature needed to achieve this "target site" temperature may vary from patient to patient. Consequently, this device will have the capacity to cool to temperatures below 0° C.

It is anticipated that there may be a slight difference, such as from about 1° to 3° C., between the coolant temperature and temperature of the cooling member outer surface. The coolant temperature will likely be low enough that the tissue adjacent to or within the surgical site will be at or slightly below freezing, for example, as low as from about 10° to about 10° C. or from about −10° C. to about 5° C., preferably from about −5° C. to about 5° C., and more preferably from about −2° C. to about 4° C.

The circulation of coolant in the cooling member is important in cardiac surgery for at least four reasons: First, the circulated coolant provides hypothermic protection to target a site where the myocardium is at the maximal ischemic risk when coronary blood flow is interrupted. Second, the temperature reduction results in myocardial hypocontraction and therefore decreased motion at the target site. This increases target site quiescence. Third, the cooled stabilizer cooling member bonds to the epicardial fat to provide enhanced traction with a minimal compressive requirement. Such bonding provides superior traction and allows for compression or retraction stabilization, as well as minimal epicardial trauma. And fourth, regional cooling induces vasospasm, which limits blood flow to the surgical site and improves visualization.

The present invention involves accessing a patient's coronary arterial system for the purpose of coronary revascularization, in which heart contractions are not artificially halted. Consistent with conventional open-chest methods, a large opening is typically provided in the patient's chest by a median sternotomy. This opening enables the surgeon to see the coronary and mammary arteries directly and to position his or her hands within the chest cavity in close proximity to these arteries for manipulation of surgical instruments. During the procedure a retractor remains in place to keep the sternum open.

According to the invention the stabilizer described above is secured in a holder attached to the sternal (or other) retractor. Preferably the holder is adjustable so that the position of the stabilizer can be adjusted relative to the retractor. Also, the stabilizer is preferably adjustable within the holder so that the lower portion of the stabilizer can be positioned on the surface of the patient's heart.

A device according to the invention can also be used for other surgical procedures, especially any surgical procedure where the cooling member is cooled sufficiently to grasp tissue. A thermostat control system will allow for precise temperature control to maximize epicardial traction while preventing freeze injury. Warmer coolant, for example, liquid or gas, can be circulated to raise the temperature in the cooling member, for example, so that grasped tissue will be released. A laparoscopic instrument according to the invention could be designed to rapidly cool and rewarm. Such an instrument would be useful instead of, for example, bowel graspers, the use of which is potentially injurious to the intestines. It is also within the scope of the invention that the device could be used in robotic surgery as well.

The scope of this invention is not limited to current surgical approaches. This device concept is easily adaptable to other surgical approaches including minimally invasive cardiac surgery techniques involving mini-thoracotomy incisions and including robotically assisted approaches.

DETAILED DESCRIPTION OF THE INVENTION

Figure 1:
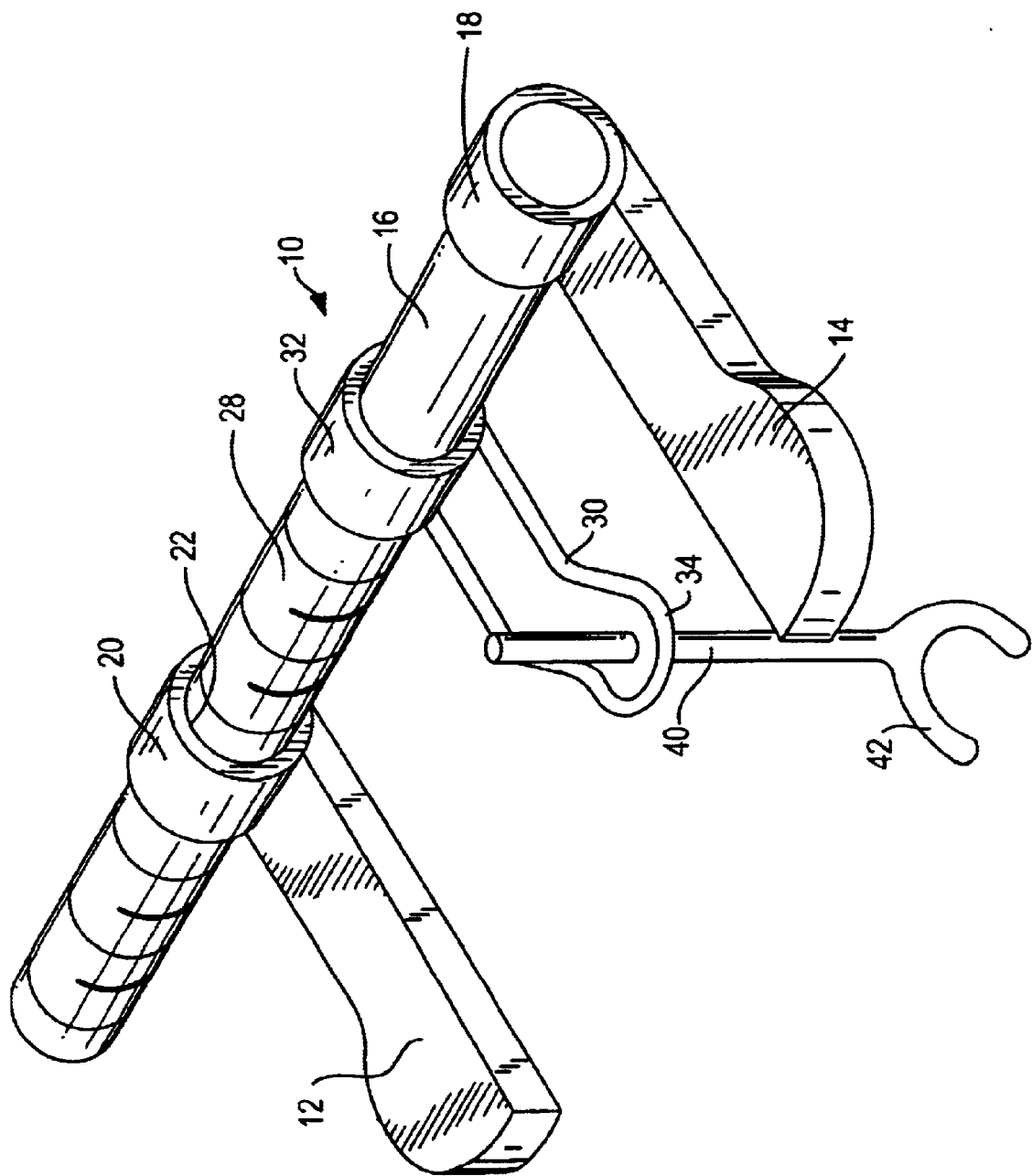
FIG. 1 is a perspective view of an OPCAB system using a stabilizer according to the invention.

The invention can perhaps be better appreciated from the drawings. An OPCAB retractor is shown in FIG. 1, where the retractor 10 comprises retractor arms 12,14 attached to threaded member 16. The proximal end 18 of retractor arm 14 is rotatably but fixedly attached to member 16, and the proximal end 20 of retractor arm 12 has an inner threaded area 22 that engages threads 28 on member 16.

A support member 30 has a proximal end 32 and a distal end 34. Proximal end 32 is fixedly attached to member 16, and distal end 34 adjustably but fixedly holds stabilizer 40, which has tubing 42.

Figure 2:
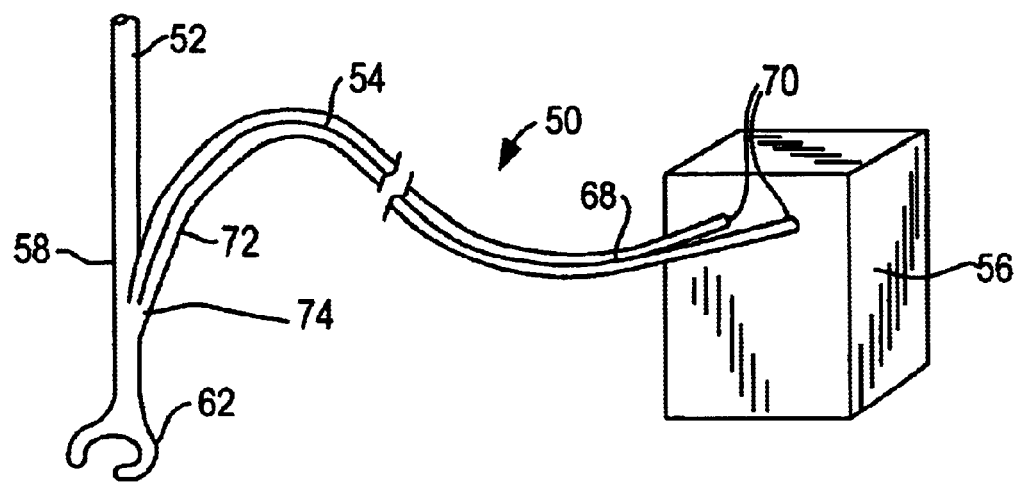
FIG. 2 is a perspective view of a stabilizer of the invention.

In FIG. 2, the stabilizer system 50 comprises a stabilizer 52 in fluid communication through tubing 54 with a cooler/pump 56. Stabilizer 52 has a shaft 58 and distal section 62. Tubing 54 has at least two lumens, which lumens can be coaxial or adjacent. Preferably tubing 54 comprises two adjacent lumens that are insulated from one another to minimize thermal impact of one coolant stream to another.

The proximal section 68 of tubing 54 is connected to ports 70 in cooler/pump 56. Cooler/pump 56 comprises cooling means to cool liquid returning through tubing 54 and then pumping cooled liquid out through tubing 54. Cooler/pump 56 could be any one of the commercially available cooling and/or pumping systems.

The distal section 72 of tubing 54 is removably connected to ports 74 in stabilizer 52.

Figure 3:
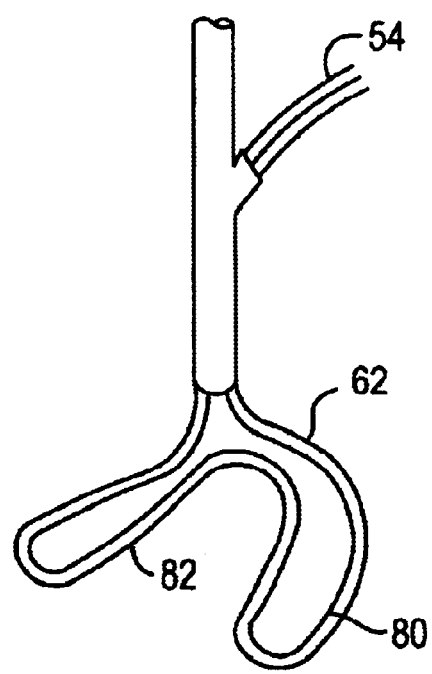
FIG. 3 is a sectional, perspective view of a device useful according to the invention.

In the sectional view shown in FIG. 3, the distal section 62 comprises hollow tubing 80 that is in fluid communication with lumens in tubing 54. A portion 82 of tubing 80 forms a substantially flat plane that is to be positioned at a surgical site (not shown). While tubing portion 82 is shown in a horseshoe-type arrangement, it is within the scope of the invention that the tubing section 82 could be circular, square, triangular, or any other desired shape.

Figure 4:
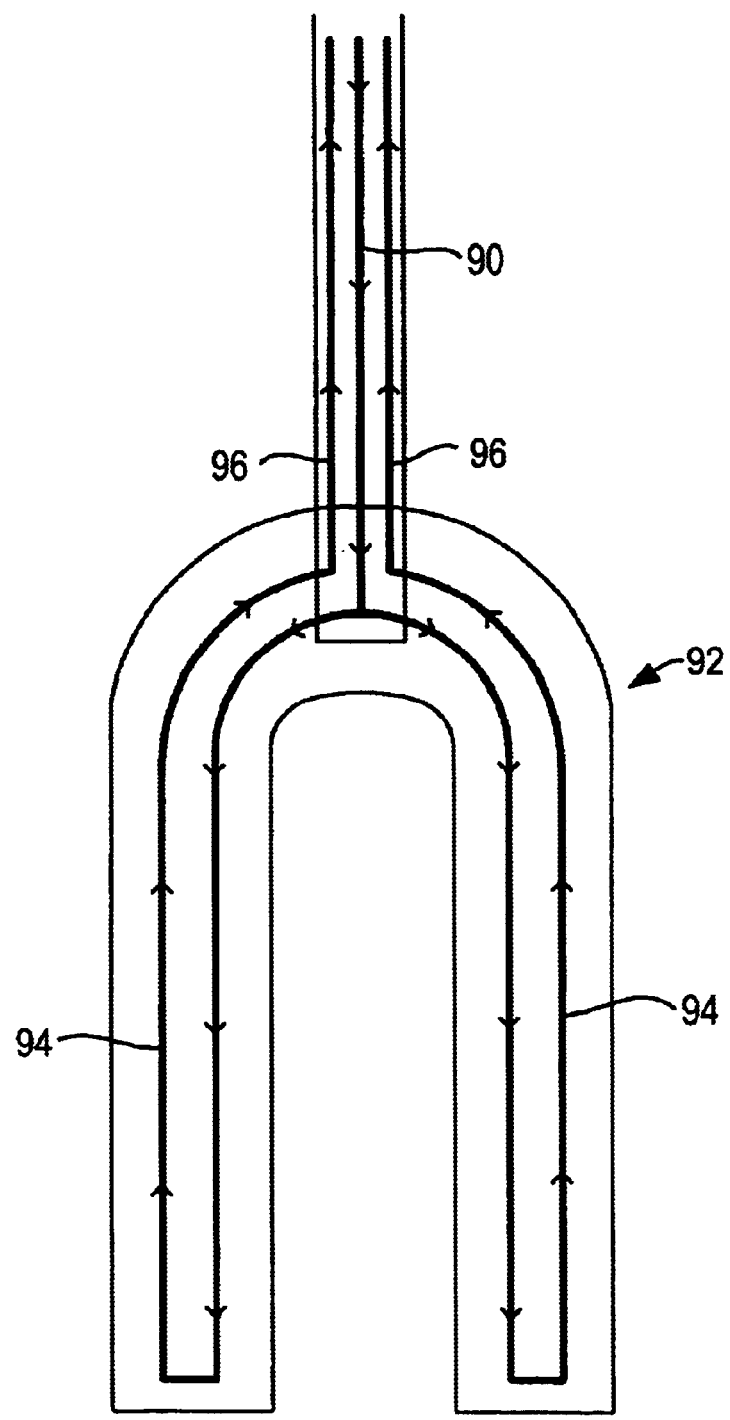
FIG. 4 is a schematic representation of a cooling system useful according to the invention.

FIG. 4 is a schematic representation of a cooled stabilizer according to the invention. In this representation coolant enters a horseshoe-shaped section 92 through a single lumen 90, which cooling fluid is directed through lumens 94 to each side of section 92 and then returns in a separate lumen 96. Either lumens 96 are combined or each lumen 96 is in fluid communication with a lumen in tubing (not shown) that extends to a cooler/pump (not shown). It is within the scope of the invention that a multiple number of pathways could be used.

It is within the scope of the invention that warm or hot liquid or fluid could be circulated in the distal end of the epicardial stabilizer. The lumen or lumens would be in fluid communication with a heating and/or cooling mechanism that would be integral with or separate from a pump.

Figure 5:
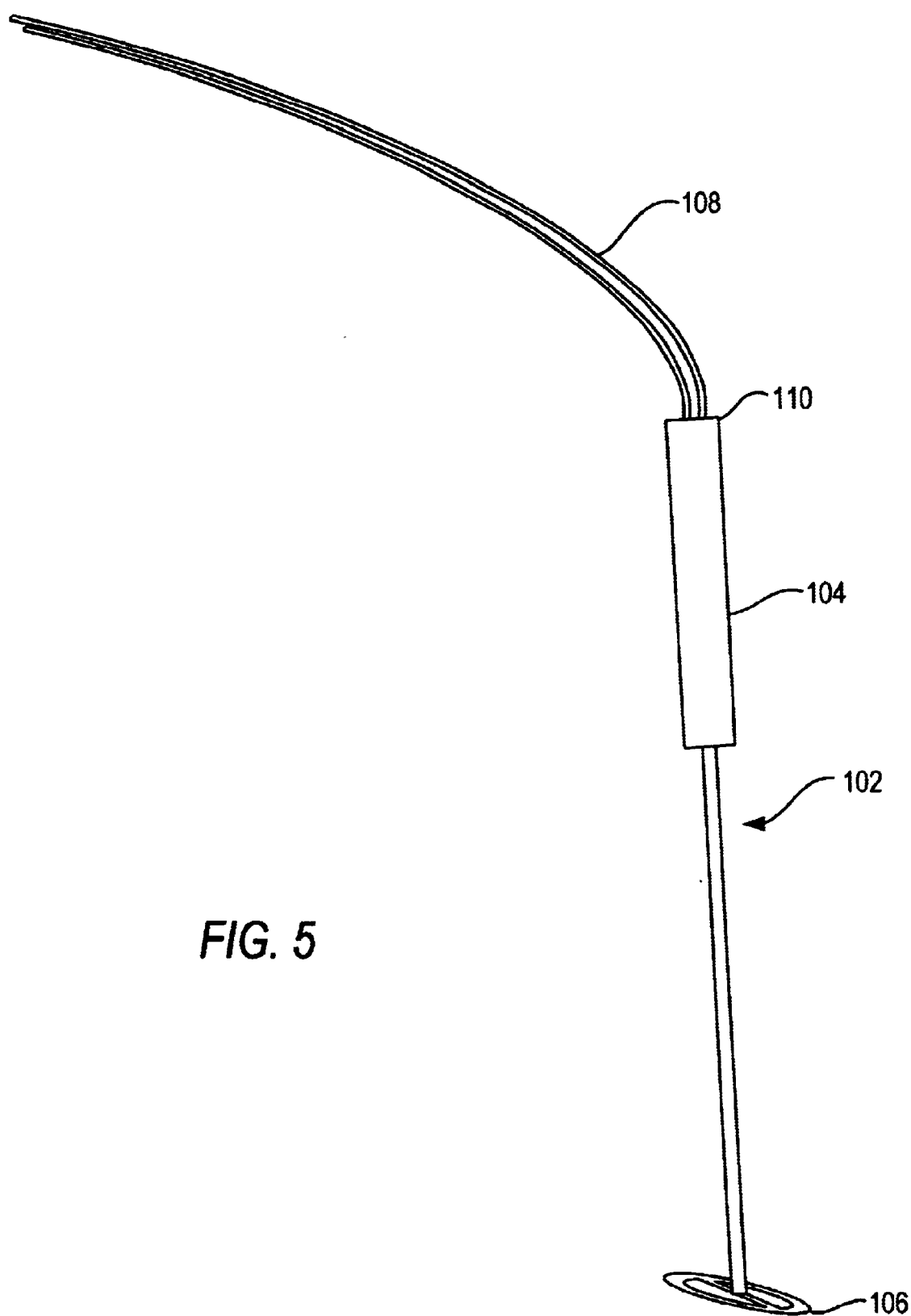
FIG. 5 is a perspective view of a laparoscopic retractor.

The hand-held laparoscopic retractor shown in FIG. 5 comprises a longitudinal member 102 having a proximal hand grip 104 and a distal cooling section or foot plate 106. Foot plate 106 is in fluid communication through one or more lumens (not shown) in longitudinal member 102 to tubing 108, which preferably enters the proximal end 110 of hand grip 104. Tubing 108 is in fluid communication with a cooling and/or heating pump system (not shown). Hand grip 104 preferably comprises hand operable controls to adjust the temperature of foot plate 106 by controlling the temperature and/or flow of fluid that flows to foot plate 106.

The apparatus shown in FIG. 5 is particularly intended to be useful in abdominal surgery, and preferably foot plate 106 would be expandable once inside the abdomen. The cooling system described would be used to rapidly cool and rewarm foot plate 106 for grasping and releasing the bowel as desired.

It is within the scope of the invention that the laparoscopic retractor of FIG. 5 will be of approximately the same dimensions as other instruments useful in laparoscopic surgical procedures. These instruments are long and slender to fit through small ports placed in the abdominal wall. The largest of these ports is about 12 mm and the smallest is about 5 mm. While the instrument could be constructed to be used through about a 5 mm port, an instrument having a diameter of about 10 to 12 mm is probably more feasible.

The materials useful in the stabilizer or retractor and the tubing can be any of the conventional, sterilizable materials useful in such applications. The tubing and the connectors therefor comprise any medically useful, flexible, polymeric or metallic materials. Preferably the tubing to the pump is a polyethylene or polybutylene polymer or copolymer. The stabilizer or retractor will preferably comprise rigid materials such as polymers or copolymers or suitable metals, and the tubing at the distal end of the stabilizer will preferably comprise a metal such as copper, aluminum, stainless steel, brass, or nitinol.

It is within the scope of the invention that for applications where precise temperature control and/or variation is important, cooling and/or heating elements would be located closer to the patient than a pump. Alternatively, a non-fluid temperature medium, such as electrical coils, could be used, for example, in conjunction with a fluid medium. In a preferred embodiment of such a device, tubing at the distal cooling member could comprise electrical, preferably low voltage, coils that would instantly or substantially instantly heat the external surface of the cooling member to allow tissue to release. Other temperature control variations are possible, including a thermostat that would adjust coolant circulation or temperature when the temperature of the coolant, the cooling member, or the tissue reaches or drops below a predetermined temperature.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. An apparatus for stabilizing tissue within a body, comprising:
   a longitudinal member having an upper portion, a lower portion, and at least one lumen within the longitudinal member,
   wherein the lower portion comprises a tissue stabilizer member to contact tissue, wherein the tissue stabilizer member is capable of being cooled to a temperature sufficiently low that the tissue stabilizer member grasps the tissue, and wherein the temperature of the longitudinal member or a portion thereof can be adjusted.

2. The apparatus of claim 1 which is suitable for surgical or laparoscopic applications.

3. The apparatus of claim 1, wherein the one or more lumens are in fluid communication with at least one part.

4. The apparatus of claim 1 which is useful for epicardial stabilization.

5. A stabilizer system for surgical or laparoscopic application which comprises an apparatus of claim 1 and a retractor.

6. The apparatus of claim 1, wherein the temperature of the stabilizer member or a portion thereof is adjusted remotely.

7. The apparatus of claim 6, wherein the at least one lumen permits fluid or gas flow.

8. The apparatus of claim 7, wherein the fluid is cooling fluid.

9. The apparatus of claim 7, wherein the longitudinal member is in fluid communication with an external fluid source.

10. The apparatus of claim 1, wherein the tissue stabilizer member comprises a plane surface.

11. The apparatus of claim 10, wherein the plane surface is substantially perpendicular to a longitudinal axis of the longitudinal member.

12. The apparatus of claim 10, wherein the tissue stabilizer member has a horseshoe shape.

13. The apparatus of claim 10, wherein the tissue stabilizer member has an annular shape.

14. The apparatus of claim 10, wherein the tissue stabilizer member has a square, rectangular, or triangular shape.

15. The apparatus of claim 10, wherein the tissue stabilizer member comprises tubing.

16. In a method for performing a surgical or laparoscopic procedure wherein tissue is contacted with an instrument to stabilize or retract said tissue, the improvement wherein said tissue is contacted with an apparatus of claim 1.

17. The method of claim 16, wherein the surgical application is coronary revascularization.

18. The method of claim 16, wherein the surgical application is laparoscopic surgery.

19. The method of claim 16, wherein the tissue adjacent to the surgical site is cooled to a temperature of about 0° C.

20. The method of claim 16, wherein the tissue adjacent to the surgical site is cooled to a temperature of from about −10° C. to 10° C.

21. The method of claim 16, wherein the tissue adjacent to the surgical site is cooled to a temperature of from about −5° to about 5° C.

22. A system for tissue stabilization in a surgical or laparoscopic application, comprising:
   a longitudinal member having an upper portion, a lower portion forming a tissue stabilizer member having a plane surface and capable of being to cooled to a temperature sufficiently low to grasp the tissue, and one or more lumens in fluid communication with at least one port, wherein the temperature of the stabilizer member or a portion thereof can be adjusted, and
   a pump in fluid communication with said at least one port.

23. The system of claim 22, wherein fluid circulated is saline solution or another physiologically acceptable fluid.

24. The system of claim 22 which also comprises a cooler for cooling fluid to be circulated in the system.

25. The system of claim 24, wherein the cooler is integral with the pump.

26. An off-pump surgical system comprising:
   a thoracic or sternal retractor;
   a support member attached to the retractor;
   a longitudinal member positioned in and supported by the support member, said longitudinal member having an upper portion, a lower portion forming a tissue stabilizer member having a plane surface and being capable of being cooled to a temperature sufficiently low to grasp the tissue, and one or more lumens in fluid communications with at least one port, wherein the temperature of the stabilizer member or a portion thereof can be adjusted;

tubing having at least two lumens and in fluid communication with at least one port of the apparatus; and a pump in fluid communication with the tubing.

27. The system of claim 26, wherein the pump cools liquid to be circulated in the system.

28. The system of claim 26, wherein the pump warms liquid to be circulated in the system.

29. The system of claim 26 which also comprises a cooler to cool liquid to be circulated in the system.

30. The system of claim 26 which also comprises a heater to heat liquid to be circulated in the system.

31. An apparatus for stabilizing tissue within a body, comprising a longitudinal member having an upper portion, a lower portion, and at least one lumen within the longitudinal member, wherein the lower portion comprises a tissue stabilizer member to contact tissue and wherein the temperature of the longitudinal member or a portion thereof can be adjusted.

32. A stabilizer system for surgical or laproscopic application which comprises an apparatus of claim 31 and a retractor.

33. A system for tissue stabilization in a surgical or laparoscopic application, comprising:

a longitudinal member having an upper portion and a lower portion forming a tissue stabilizer member having a plane surface and capable of being to cooled to a temperature sufficiently low to grasp the tissue, wherein the temperature of the longitudinal member or a portion thereof can be adjusted; and a pump in fluid communication with said at least one port.

34. An off-pump surgical system comprising:

a thoracic or sternal retractor;

a support member attached to the retractor;

a longitudinal member positioned in and supported by the support member, said longitudinal member having an upper portion and a lower portion forming a tissue stabilizer member having a plane surface and being capable of being cooled to a temperature sufficiently low to grasp the tissue, wherein the temperature of the longitudinal member or a portion thereof can be adjusted;

tubing having at least two lumens and in fluid communication with at least one port of the apparatus; and a pump in fluid communication with the tubing.

35. In a method of performing a laproscopic procedure wherein tissue is contacted with an instrument to stabilize or retract tissue, the improvement wherein said tissue is contacted with an apparatus comprising a longitudinal member having an upper portion, a lower portion, and at least one lumen within the longitudinal member, wherein the lower portion comprises a tissue stabilizer member to contact tissue and wherein the tissue stabilizer member is capable of being cooled to a temperature sufficiently low that the tissue stabilizer member grasps the tissue.

* * * * *